United States Patent
Bradshaw

[11] Patent Number: 6,051,832
[45] Date of Patent: Apr. 18, 2000

[54] DRIFT CHAMBERS

[75] Inventor: Robert Fagan Donat Bradshaw, Warminster, United Kingdom

[73] Assignee: Graseby Dynamics Limited, London, United Kingdom

[21] Appl. No.: 09/212,906

[22] Filed: Dec. 16, 1998

Related U.S. Application Data

[63] Continuation of application No. PCT/GB97/02239, Aug. 20, 1997.

[30] Foreign Application Priority Data

Aug. 20, 1996 [GB] United Kingdom .................. 9617409

[51] Int. Cl.[7] ............................. B01D 59/44; H01J 49/00
[52] U.S. Cl. ........................................... 250/286; 250/281
[58] Field of Search .................................. 250/281, 286, 250/287

[56] References Cited

U.S. PATENT DOCUMENTS

| | | | |
|---|---|---|---|
| 2,387,550 | 10/1945 | Winkler . | |
| 3,596,088 | 7/1971 | Cohen et al. . | |
| 4,777,363 | 10/1988 | Eiceman et al. | 250/287 |
| 4,855,595 | 8/1989 | Blanchard | 250/288 |
| 5,420,424 | 5/1995 | Carnahan et al. . | |
| 5,789,745 | 8/1998 | Martin et al. | 250/286 |
| 5,834,771 | 11/1998 | Yoon et al. | 250/286 |

FOREIGN PATENT DOCUMENTS

| | | |
|---|---|---|
| 0 253 155 A1 | 1/1988 | European Pat. Off. . |
| 195 13 459 A1 | 1/1996 | Germany . |

OTHER PUBLICATIONS

International Search Report.

*Primary Examiner*—Bruce C. Anderson
*Attorney, Agent, or Firm*—Wallenstein & Wagner, Ltd.

[57] ABSTRACT

A drift chamber for an ion mobility spectrometer includes an array of conductive electrodes (12, 14, 16, 18) mounted upon a common insulating substrate (10) such as a printed circuit board. The printed circuit board may also form one side of a rectangular enclosure (24), thus allowing the drift chamber to be substantially smaller than previously. The printed circuit board may have a track (60) around its periphery to which the rectangular enclosure (24) can be attached, thus creating a gas-tight seal.

20 Claims, 4 Drawing Sheets

FIG. 1a
FIG. 1c
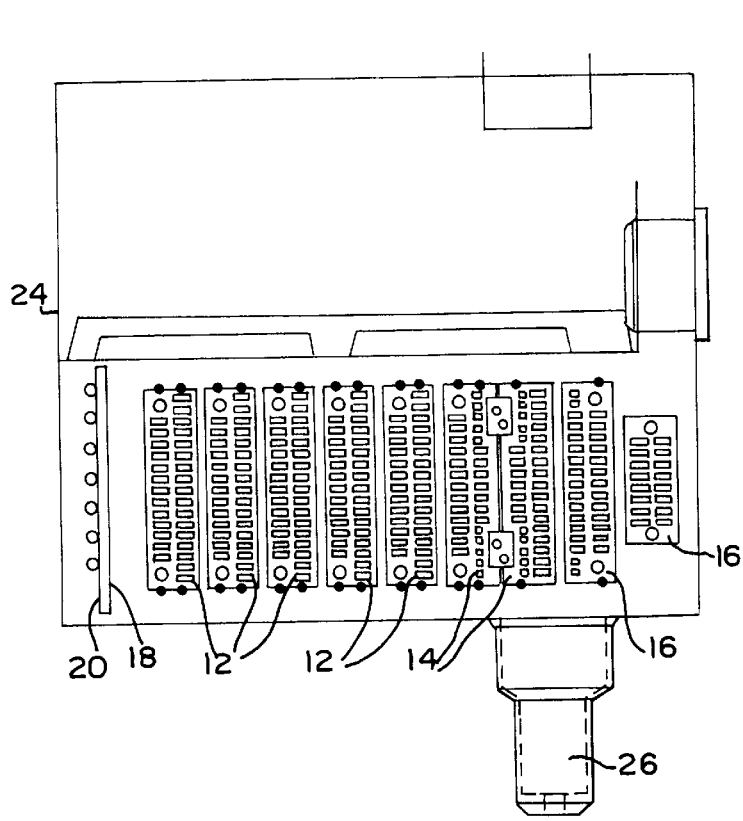
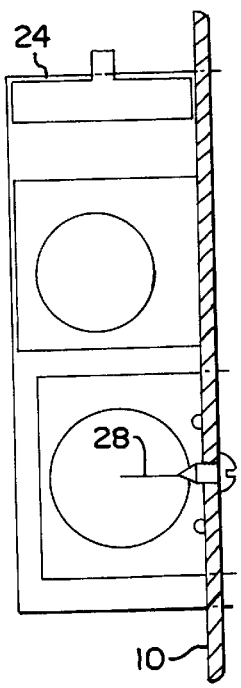
FIG. 1b
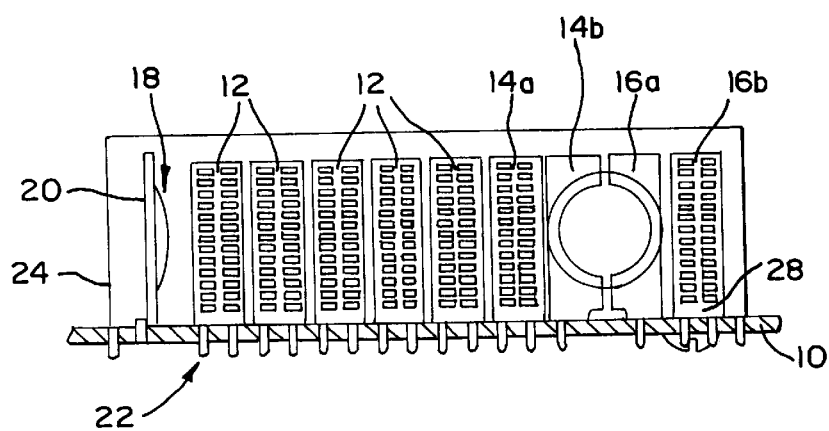

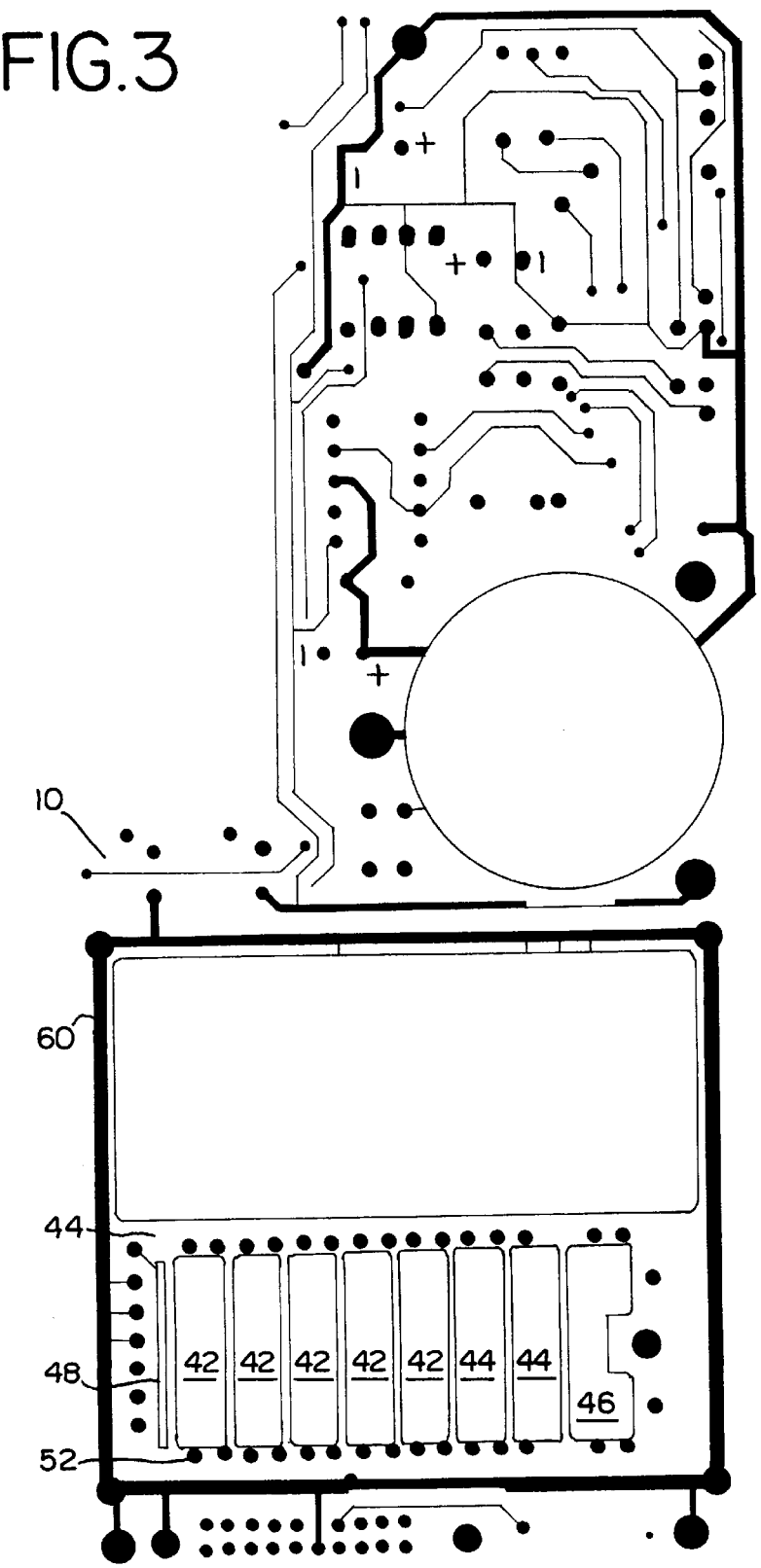

DRIFT CHAMBERS

This is a continuation of PCT/GB97/02239, filed Aug. 20, 1997.

The present invention relates to drift chambers or drift tubes for use, for example, in ion mobility spectrometers.

BACKGROUND OF THE INVENTION

Such drift chambers consist conventionally of a linear array of conducting electrodes, which may take various forms, electrically insulated from one another, and held at various suitable electrical potentials in order to create appropriate electric fields in the spaces between them, usually along the axis of the tube.

The electrode array is normally enclosed in a cylindrical gas-tight chamber furnished with openings through which sample vapours or gases, and circulating carrier gas, may be introduced.

Ion mobility spectrometers may be used to detect the presence in an ambient atmosphere of gases or vapours arising from of substances of interest e.g explosives, drugs, and organic pollutants of various types.

An ion mobility spectrometer (IMS) will typically comprise an ionization source, a reaction region, a drift tube, a gating, or injection, grid between the reaction region and the drift space, and an ion detector, coupled to a collector electrode within the drift chamber.

The modus operandi of ion mobility spectrometers is well known. Briefly, a carrier gas, typically dry air, is introduced into the spectrometer together with the sample gas or vapour, and is fed via an inlet to the reaction region containing an ionization source such as nickel 63 or a corona ionization element, resulting in a partial ionisation of the molecules of the carrier gas and the sample. Additional charge may also be transferred by impact from carrier gas molecules to sample molecules.

Within the reaction region a potential gradient is usually present, moving the charged mixture of sample and carrier molecules towards the injection grid. The grid is held at a potential such as to block transfer of the charged mixture to the drift chamber except when the potential is periodically reduced, thereby permitting a package or "pulse" of ions to enter the drift chamber.

Within the drift chamber an approximately constant potential gradient, arising as a result of the potentials is applied to the successive electrodes of the electrode array, moves the injected ions towards a collector electrode, located at the end of the drift chamber remote from the reaction region, where the ion charges are collected.

The time of arrival of the ions with respect to the opening of the injection grid is dependent on the mobility of the ions, light ions reaching the collector electrode sooner than heavier ones. The identity of the ions, and hence of the original molecules and of the substances, may be established by reference to the time of flight within the drift chamber, and the relative concentration of the ions, and hence of the molecules and of the substances, by reference to the magnitude of the respective collector currents. The opening of the injection grid is usually made periodic to increase the signal-to-noise ratio of the system, or in order to perform a continuing series of measurements.

To realise an IMS drift chamber the various electrodes must be supported in their correct relative positions, insulated from one another, and supplied with the appropriate voltages.

In the past various different constructional methods have been adopted. However many have involved a "stack" of annular metallic electrodes separated by insulators. Such a "stack" may be threaded on to two or more columns, or, in some cases, the insulators may be configured to locate the electrodes and the whole stack placed under axial compression.

The cell contained within such a stack may be hermetically sealed from the surrounding atmosphere by nature of its construction e.g by the use of compressible insulators between the electrodes.

In general each electrode will need to be held at a unique electrical potential; in some cases this potential will be time-variable to provide a gating function. It is most convenient if each electrode is supplied with its own connection to circuitry outside the containment, but this will usually involve numerous gas-tight lead-throughs for the drift chamber, at least some of which will need to operate at high potential.

Ion mobility spectrometers using drift tubes such as described above tend to be relatively expensive to build because of the need for precision machined components, the complex assembly operations involved, and the multiplicity of electrical connections.

SUMMARY OF THE INVENTION

According to the present invention, there is provided a drift chamber suitable for use in an ion mobility spectrometer, comprising a plurality of electrically conductive electrodes, characterized in that the electrodes are mounted on a planar insulating substrate.

Employing a planar substrate confers several advantages. Firstly, manufacture is simplified relative to the previous drift tube described above, thus reducing cost, as the separate insulating rods must be carefully located between the electrodes and then held in place by compression. Secondly, the planar substrate allows a significantly smaller, flatter drift chamber to be produced relative to previous chambers, which in turn permits miniaturization of the IMS. For example, the drift chamber may further comprise an enclosure, at least some of the electrodes being within the said enclosure, the dimensions of the enclosure perpendicular to the plane of the substrate being smaller than the dimensions of the enclosure parallel to the plane of the substrate.

Preferably, the enclosure is generally rectangular, although a truncated cylinder, the diameter of which is larger than the height of the cylinder, may be envisaged.

Preferably, the substrate constitutes one wall of the enclosure. This further permits miniaturisation of the drift chamber, as the lead throughs from the electrodes to, for example, ancillary electronic components to generate suitable electrode potentials can pass through the substrate itself.

Previously, the drift chamber consisted of an array of electrodes within a completely separate enclosure, and additional, separate apertures within that enclosure were therefore necessary.

The electrodes may be mounted upon the insulating substrate by means of integral legs or pins which may be positioned in, and mechanically attached and electrically connected, for example by soldering or brazing, to conductive apertures in the insulating substrate, for example into through-plated holes in a double-sided printed circuit board, such as a double-sided copper-clad glass-reinforced resin printed circuit board, the mounted electrodes being upstanding from the surface of the board and separated, and insulated, one from another, by an intermediate space.

Of course, the planar substrate need not be of unitary construction. However, one convenient form of substrate is a printed circuit board.

In the preferred arrangement, therefore, gas tight lead throughs from the electrodes to ancillary electronics are conveniently, and cheaply, provided by holes in the printed circuit board into which the pins on the electrodes may be soldered. In other words, when the pins or legs are secured into the-apertures therein there is a gas-tight connection between the one face of the substrate upon which the electrodes are mounted, and the other face.

Further, the relative positions of the electrodes may be accurately defined by the locations of the conductive apertures in which the legs or pins are located and secured. The electrically conductive metal pads around the apertures may be electrically isolated from the surrounding conductive regions upon the substrate, by regions from which the conductive material has been removed.

The pads to which the legs or pins of the electrodes connect on the other face of the substrate may be connected to ancillary electronics, such as to sources of bias potential for the electrodes, or for example to voltage-defining components, such as elements of a resistor chain connected across a source of bias potential, which elements may be mounted on the substrate in the form of conventional or surface-mounted components.

Preferably, the enclosure consists of or includes a conductive material. In one form, the enclosure is sheet metal. Using a conductive material provides screening for the sensitive electronics associated with the collector electrode.

The enclosure may itself be located upon the substrate to enclose the upstanding electrodes, by means of pins or legs engaging in apertures in the substrate, for example in through-plated holes.

The necessary sealing of the enclosure to the substrate may be effected by soldering the edges of the sheet metal from which the enclosure is optionally formed to corresponding conductive areas upon the substrate or alternatively by means of a suitable sealant material.

Gas entry—carrier and sample flows—to the sealed enclosure may be provided through ports in the enclosure, or through apertures in the substrate.

The use of such a construction enables a low-cost, lightweight, drift chamber for an ion mobility spectrometer to be readily manufactured using conventional electronic circuitry manufacturing techniques, such a drift chamber being inherently suitable for physical integration with the electronic circuitry necessary for its operation. In addition, the electrodes can be readily and relatively cheaply formed in the flat using photolithography techniques, and then folded into the required shape. Electrodes formed in such a way are inherently suitable for soldering to printed circuit boards.

For example, the electrodes that form the drift chamber according to the present invention may be made relatively small, typically 15 mm×10 mm×5 mm. It is thus possible to construct an IMS that contains all the electronic and electrical components necessary for operation that is little larger than a pocket calculator.

The invention is described, by way of example only, with reference to the accompanying drawings of which:

BRIEF DESCRIPTION OF THE DRAWINGS

FIGS. 1a, 1b, and 1c show respectively the plan, side-elevation and end-elevation (with the surrounding enclosure cut away) of one form of drift chamber in accordance with the invention, incorporated in a small portable IMS instrument;

FIG. 3 shows a portion of one face of a printed circuit board on which such electrodes may be mounted.

DETAILED DESCRIPTION OF THE PREFERRED

Figure 2A:
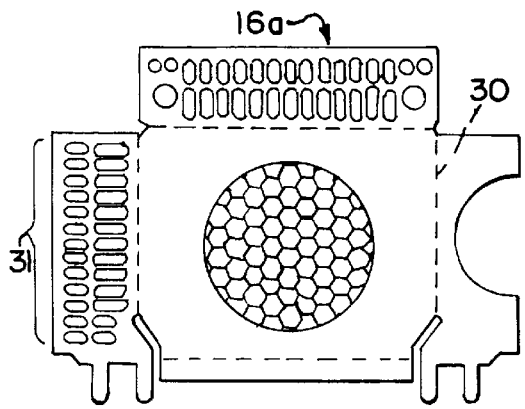
FIGS. 2a–2f show the various electrode elements used in the drift chamber of FIG. 1.

Referring to FIG. 1 of the drawings, a double-sided printed circuit board 10 carries a series of metal foil or sheet electrodes of differing types, which together constitute a drift chamber for the ion mobility spectrometer carried upon the board 10.

Electrodes 12 are identical field-defining electrodes, electrodes 14a and 14b together constitute a gating grid, and electrodes 16a and 16b together constitute ionising region electrodes, for the drift chamber.

Electrode 18 is the collector electrode for the drift chamber, mounted upon and directly associated with a signal amplifier, not shown, carried upon ancillary printed circuit board 20.

Each electrode is mechanically supported by integral pins or legs, such as 22, which also serve to provide electrical connection between the electrodes and the appropriate conductive parts of the printed circuit board 10.

The whole assembly is contained within a sheet metal gas-tight enclosure 24, which is sealed to the upper surface of the printed circuit board 10 by being soldered along the periphery of its lower, open end to a corresponding metallised track upon printed circuit board 10.

Within the enclosure 24 a sieve is employed. This contains a desiccant to dry the air as it flows through the drift chamber. A miniature fan may also be attached to the enclosure 24, to circulate the air in the opposite direction to that of the electron flow in the drift chamber. Also shown, in outline, is the sample inlet aperture 26 for the instrument, serving to lead sample gases and vapours into the reaction region of the instrument, and a corona ionising electrode 28. This may be formed as part of the enclosure 24.

The configuration of the various drift chamber electrodes, in the flat, prior to being bent along the indicated dotted lines, such as 30, to form their final three-dimensional configurations, are shown in FIGS. 2a to 2e respectively.

The electrodes shown in FIG. 2 are fabricated in the flat in their entirety from sheet brass of thickness 0.006 inches (150 µm), including all apertures, wires and meshes, by means of a standard photo-etching process.

The brass electrodes are suitably metal plated. The field-defining electrodes are tin plated, whereas the gating grid electrodes 14a and 14b are gold plated, to minimise the chance of insulating surface layers forming and disturbing the action of the grids due to surface charges on the layers.

FIG. 2a shows an electrode 16a which constitutes one part of the ionizing region electrodes, prior to being bent into the final three dimensional structure. As previously mentioned, the flat metal electrode in FIG. 2a is formed from sheet brass which is patterned with photoresist and etched to form the desired shape. The dotted lines 30 shown in FIG. 2a are in practice score lines formed by partial etching of the brass sheet. The score lines assist in folding the flat electrode into its final, generally box-like shape.

Holes 31 are also etched into the brass sheet. These serve to improve air flow through the drift chamber and to assist the drying action of the sieve.

Figure 2B:
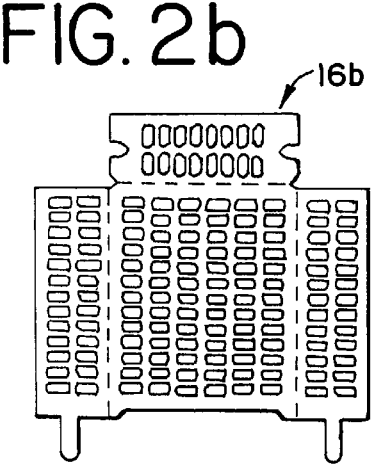

FIG. 2b shows an electrode 16b which constitutes the other part of the ionizing region electrodes, again prior to being bent into its final three dimensional shape.

Figure 2C:
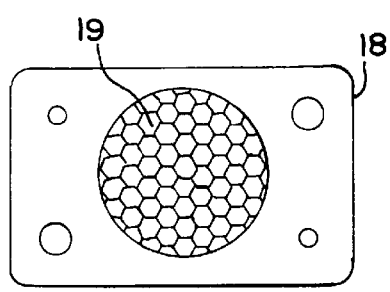
Figure 2D:
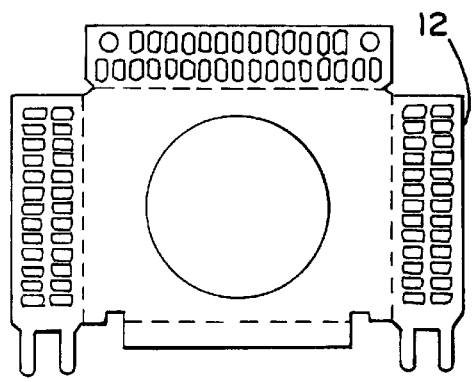

FIG. 2c shows, in plan view, the collector electrode 18. The mesh 19 screens the electrode from the induced currents generated by the approaching ion pulse, and is a domed honeycomb shape to improve its rigidity. FIG. 2d shows, again in the flat, one of the field-defining electrodes 12. As with the other electrodes, holes 31 are provided to improve air flow through the drift chamber.

Figure 2E:
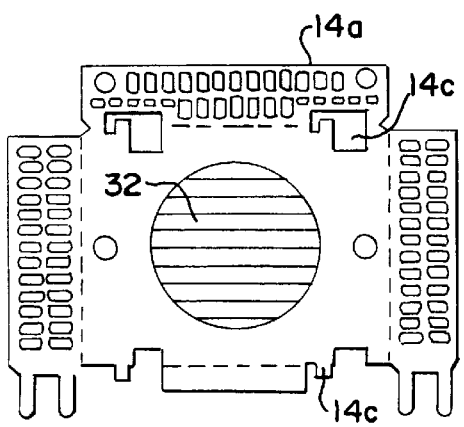
Figure 2F:
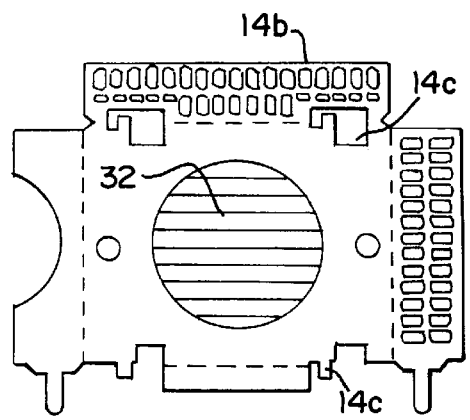

FIGS. 2e and 2f show, respectively, the two parts of the gating grid, in the flat. Each includes a row of wires 32 which are, as previously described, generated by etching a brass sheet.

The two parts 14a and 14b of the gating grid are assembled together mechanically, but electrically insulated from one another, by means of an intermediate insulating layer. The two parts are shown in FIGS. 2e and 2f respectively. Each comprises tabs such as 14c which are bent over to secure each part to an intermediate insulator of melamine, or for higher, temperature applications, of mica. Alternatively the two parts 14a and 14b may be held together by a double-sided adhesive interlayer to which each is caused to adhere.

Figure 4:
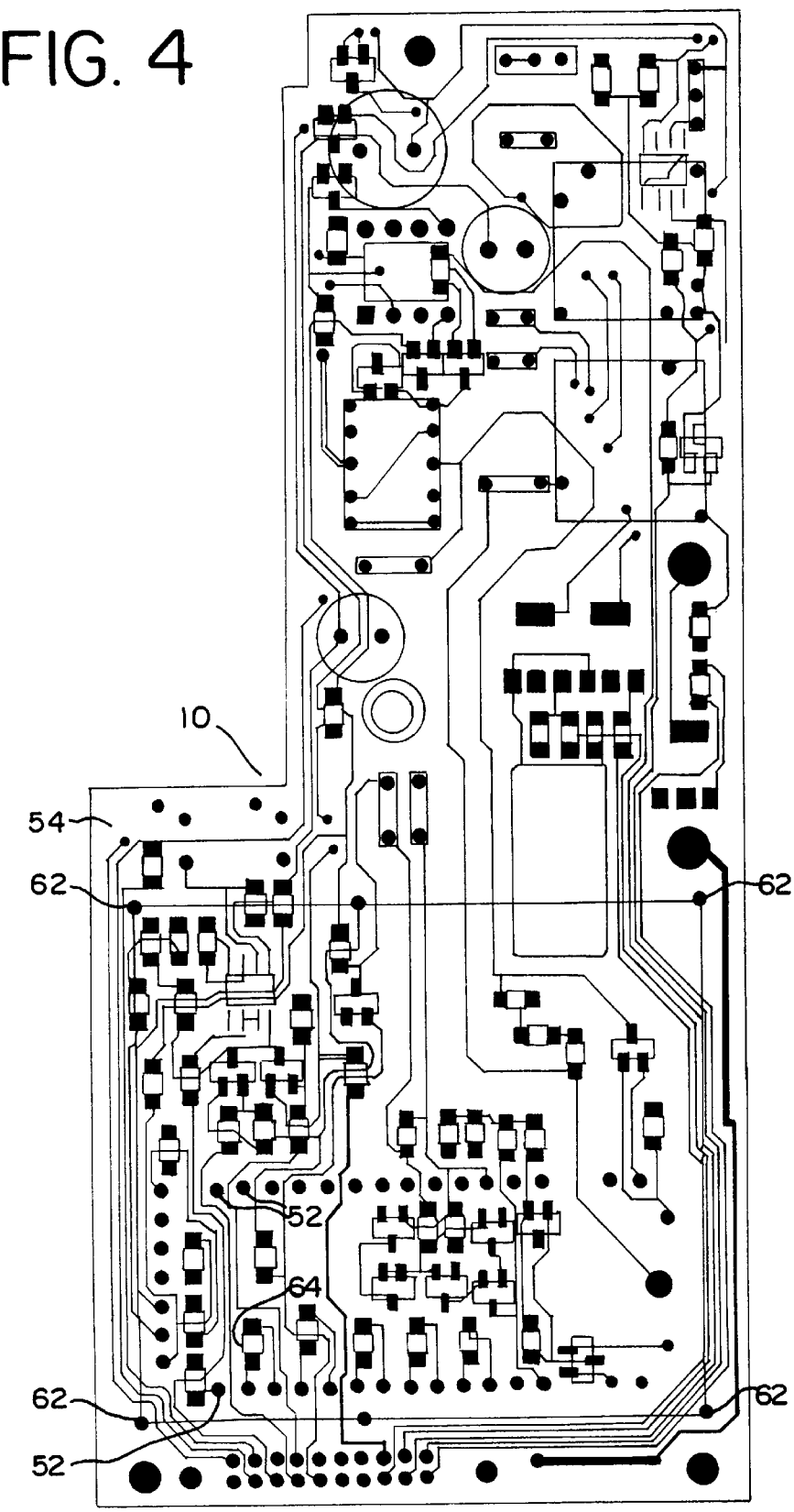
FIG. 4 shows the corresponding portion of other face of the printed circuit board of FIG. 3.

The opposed upper and lower sides of a double-sided printed circuit board 10 which carries the drift chamber are shown in FIGS. 3 and 4 respectively.

Referring to FIG. 3, a series of conductive areas 42, 44, 47 and 48 is shown upon the upper face 40 of the printed circuit board 10. Each conductive area corresponds to, and forms the lower conductive face 20 respectively, of one of the various electrode structures 12, 14, 16, 18, shown in FIG. 1. The conductive areas are connected to related, adjoining, through-plated holes, such as 52, into which the pins or legs such as 22, of the respective electrodes are soldered. A connection between the conductive areas and their respective electrodes, and, through the through-plated holes, to circuitry upon the lower face 54 of the board 10 is thereby provided.

The broad conductive track 60, upon the upper face 40 of board 10, provides the surface to which the periphery of the lower, open, end of the sheet metal enclosure 24 is soldered, to enclose the assembled drift chamber. The enclosure may be provided with downwardly extending pins to provide location, such pins engaging in holes in board 10 shown as 62 in FIG. 4.

Associated with, and connected to, the plated through holes into which the electrodes mount, are a series of surface mounted resistors, such as 64, carried upon the lower face, 54, of board 10, together forming a potential divider chain to provide appropriate potentials, from a DC source connected across the chain, to the electrodes carried upon the upper face 44 of the board.

Various modifications may be made to the construction of drift chamber shown, which represents only one embodiment of a drift chamber and ion mobility spectrometer in accordance with the invention, without exceeding the scope of the invention.

Numerous advantages accrue from use of drift chambers constructed in accordance with the invention, including:

low component cost due to the use of established photo-etching and printed circuit board construction techniques;

low assembly cost due to conventional electronic industry component location and assembly;

electrical feed-throughs and interconnections established automatically in construction and assembly;

design changes simple to implement; and the resulting drift chamber structure is light and rigid, making it particularly suitable for personal and portable IMS instruments.

A further advantage of the relatively small dimensions of the drift chamber is that an IMS can be constructed with two drift chambers, the overall dimensions of the IMS still being small enough to be hand or palm held. Using two drift chambers allows the IMS to detect both positively and negatively charges ions, without having to carry out any adjustments to the device. For example, the control circuitry for the IMS (not shown) can be programmed to switch rapidly between the two drift chambers, and give a real time indication of the presence of both positively charged ions, such as nerve agents, and negatively charged ions, such as most explosives and mustard gas.

Although an embodiment of the invention has been described in which the drift chamber is mounted upon a printed circuit board, it will be appreciated that the term "printed circuit board or the like" used above, encompasses other similar forms of circuit carrier such as for example, without limitation, ceramic or insulated metal substrates bearing conductive patterns applied to them in any known manner. Similarly although reference is made to "plated through-holes" in such circuit carriers, the conductive layers in such through-holes may be provided in other ways, such as by metallisation. Methods other than soldering, for example brazing, appropriate to the nature of the substrate and the conductive material of the circuit board, may also be employed to electrically and mechanically attach the pins 22 to the conductive material of the through-holes in the circuit carrier.

It will be appreciated that in putting the invention into effect methods of construction and the materials employed therefor should be such as not to introduce into the completed drift chamber or ion mobility spectrometer any substances giving rise to gases or vapours, even in trace quantities, likely to interfere with the proper operation of the instrument.

The invention claimed is:

1. A drift chamber for use in an ion mobility spectrometer comprising: an enclosure, a substantially planar electrically insulating substrate therein, and a plurality of electrically conductive electrodes mounted on the substrate for creating electric fields within the enclosure, wherein the electrodes extend out of the plane of the substrate and along an axis of the drift chamber.

2. A drift chamber as claimed in claim 1, wherein at least some of the electrodes are within said enclosure, the dimensions of the enclosure perpendicular to the plane of the substrate being smaller than the dimensions of the enclosure parallel to the plane of the substrate.

3. A drift chamber as claimed in claim 2, wherein the enclosure is generally rectangular.

4. A drift chamber as claimed in claim 2, wherein the substrate constitutes one wall of the enclosure.

5. A drift chamber as claimed in claim 2, wherein the substrate forms a gas tight seal with the enclosure.

6. A drift chamber as claimed in claim 1, wherein the substrate includes a plurality of conductive apertures arranged to receive the electrodes.

7. A drift chamber as claimed in claim 6, wherein the electrodes include integral legs arranged to enter the conductive apertures in the substrate.

8. A drift chamber as claimed in claim 6, in which the electrodes are attached to the conductive apertures with solder.

9. A drift chamber as claimed claim 1 wherein the insulating substrate carries conductive patterns.

10. A drift chamber as claimed in claim 9 wherein the insulating substrate is a printed circuit board.

11. A drift chamber as claimed in claim 10, wherein the printed circuit board is printed on both sides.

12. A drift chamber as claimed in claim 10 wherein the printed circuit board is a double sided copper and glass reinforced resin printed circuit board.

13. A drift chamber as claimed in claim 2, wherein each of the electrodes are located within the enclosure on a first planar face of the substrate, electronic components being located on a second planar face of the substrate.

14. A drift chamber as claimed in claim 13, wherein the electronic components include sources of bias potential for biasing the electrodes.

15. A drift chamber as claimed in claim 13, wherein the electronic components include components for providing a voltage on at least some of the electrodes for biasing the electrodes.

16. A drift chamber as claimed in claim 15, wherein the components for providing a voltage on at least some of the electrodes for biasing the electrodes are a resistor chain connected across a source of bias potential.

17. A drift chamber as claimed claim 13, wherein the electronic components are electrically connected to the electrodes through the substrate.

18. A drift chamber as claimed in claim 1, wherein the electrodes are brass.

19. A drift chamber as claimed in claim 18, wherein at least some of the electrodes are coated with tin.

20. A drift chamber as claimed in claim 18, wherein the brass electrodes are coated with gold.

* * * * *